(12) United States Patent
Datt et al.

(10) Patent No.: US 10,124,084 B2
(45) Date of Patent: Nov. 13, 2018

(54) READY TO USE BIODEGRADABLE AND BIOCOMPATIBLE DEVICE AND A METHOD OF PREPARATION THEREOF

(71) Applicant: Datt Mediproducts Limited, New Delhi (IN)

(72) Inventors: Rajan Datt, New Delhi (IN); Ramadhar Kumar, New Delhi (IN); Pallavi Shrivastava, New Delhi (IN)

(73) Assignee: Datt Life Sciences Private Limited, Kolkata, West Bengal (IN)

( * ) Notice: Subject to any disclaimer, the term of this patent is extended or adjusted under 35 U.S.C. 154(b) by 72 days.

(21) Appl. No.: 14/441,125

(22) PCT Filed: Aug. 21, 2014

(86) PCT No.: PCT/IN2014/000536
§ 371 (c)(1),
(2) Date: May 6, 2015

(87) PCT Pub. No.: WO2015/145457
PCT Pub. Date: Oct. 1, 2015

(65) Prior Publication Data
US 2016/0339140 A1 Nov. 24, 2016

(30) Foreign Application Priority Data
Mar. 24, 2014 (IN) .............................. 838/DEL/2014

(51) Int. Cl.
*A61L 15/44* (2006.01)
*A61L 15/42* (2006.01)
*A61L 15/14* (2006.01)
*A61L 15/64* (2006.01)
*A61F 13/00* (2006.01)
*A61L 15/28* (2006.01)
*A61L 15/32* (2006.01)

(52) U.S. Cl.
CPC ...... *A61L 15/425* (2013.01); *A61F 13/00063* (2013.01); *A61L 15/14* (2013.01); *A61L 15/28* (2013.01); *A61L 15/32* (2013.01); *A61L 15/44* (2013.01); *A61L 15/64* (2013.01); *A61L 2300/418* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 8,038,991 B1 * | 10/2011 | Stankus | A61K 31/00 424/530 |
| 2006/0189516 A1 * | 8/2006 | Yang | A61L 27/20 514/16.5 |
| 2011/0218472 A1 | 9/2011 | Mirzadeh et al. | |
| 2011/0311608 A1 | 12/2011 | Roorda et al. | |
| 2012/0149111 A1 * | 6/2012 | Wegst | C12N 5/0619 435/395 |

FOREIGN PATENT DOCUMENTS

| | | | |
|---|---|---|---|
| CN | 101954117 A | * | 1/2011 |
| WO | WO-2012017415 A2 | | 2/2012 |

OTHER PUBLICATIONS

English translation of CN101954117A retrieved from Espacenet on Jan. 31, 2017.*
International Search Report Issued in PCT/IN2014/000536 dated Feb. 6, 2015.

* cited by examiner

*Primary Examiner* — Jessica Worsham
(74) *Attorney, Agent, or Firm* — Allen, Dyer, Doppelt + Gilchrist, PA

(57) ABSTRACT

The invention provides a ready to use biodegradable and biocompatible device and a method for manufacturing thereof. The device of present invention is a novel porous scaffold which can be used as carrier of plurality of therapeutics to quickly stop bleeding and other biomaterial and biomedical application. The scaffold can be directly applied to the spot of the wound and will stop bleeding within no time. The scaffold of the present invention comprises of combined application of air dry and freeze dry method. The scaffold also comprises of excellent ventilations properties and easy removal of the scaffold without causing any extra hemorrhage to the wound.

5 Claims, 4 Drawing Sheets

Diagram Description
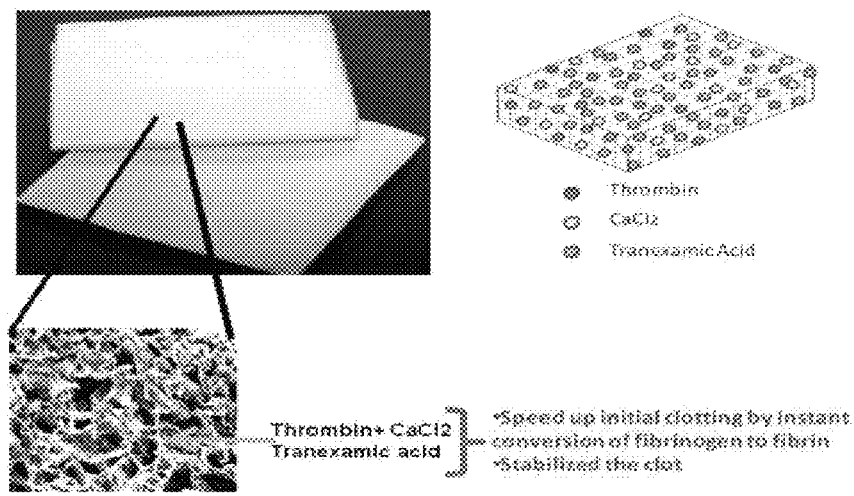
Fig. 1 shows the matrix and its micro structure with vesicular voids. The schematic diagram shows the constituents are held in the matrix of DLS Haemostat.
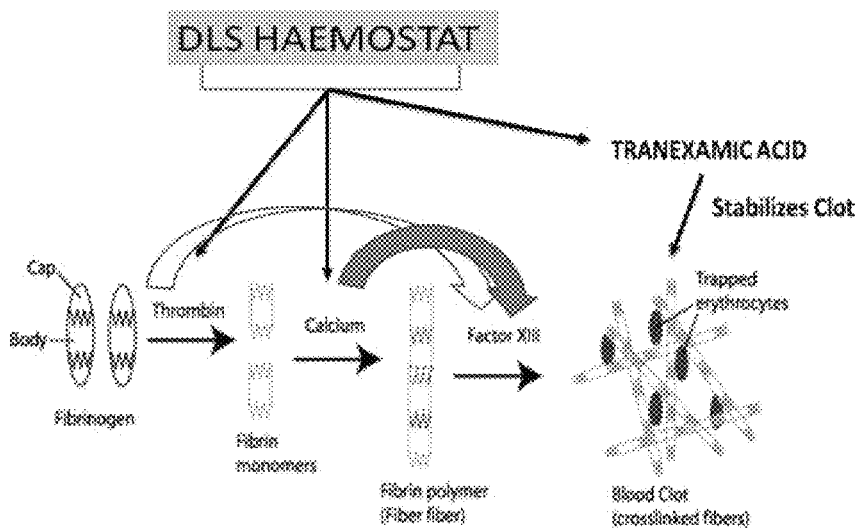
Fig. 2 shows the Schematic representation-Constituents of DLS Haemostat scaffold and the coagulation cascade.

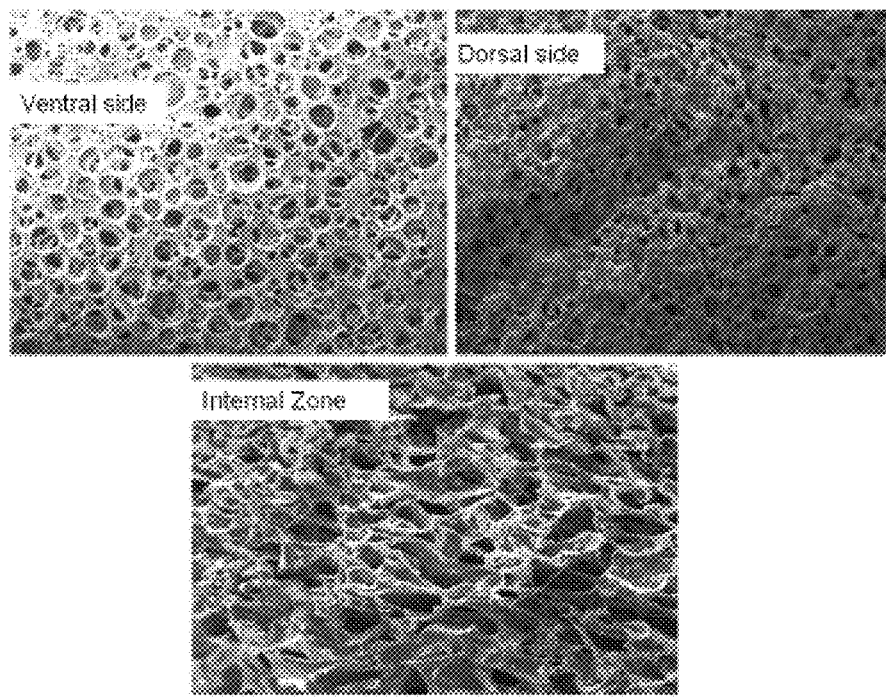
Fig. 3 shows the SEM photographs of the device showing differential porosity and pore size.
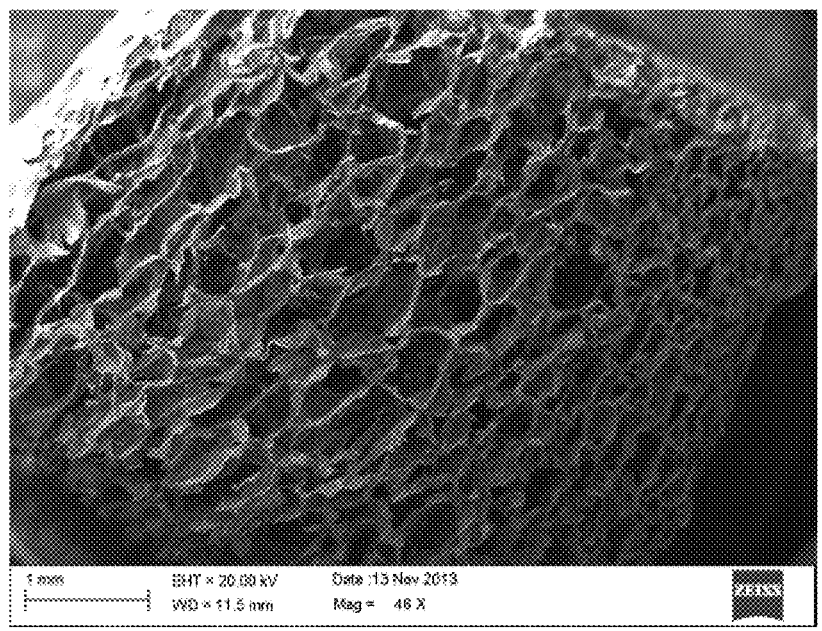
Fig. 4 shows the SEM photograph of the scaffold without drug.

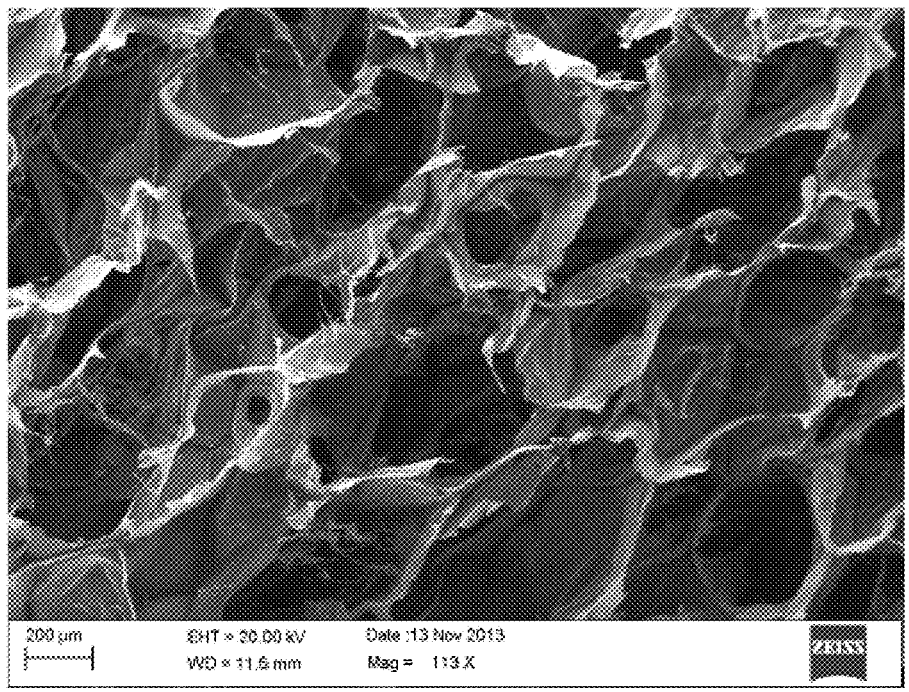
Fig. 5 shows the close magnified SEM photograph of the scaffold without drug.
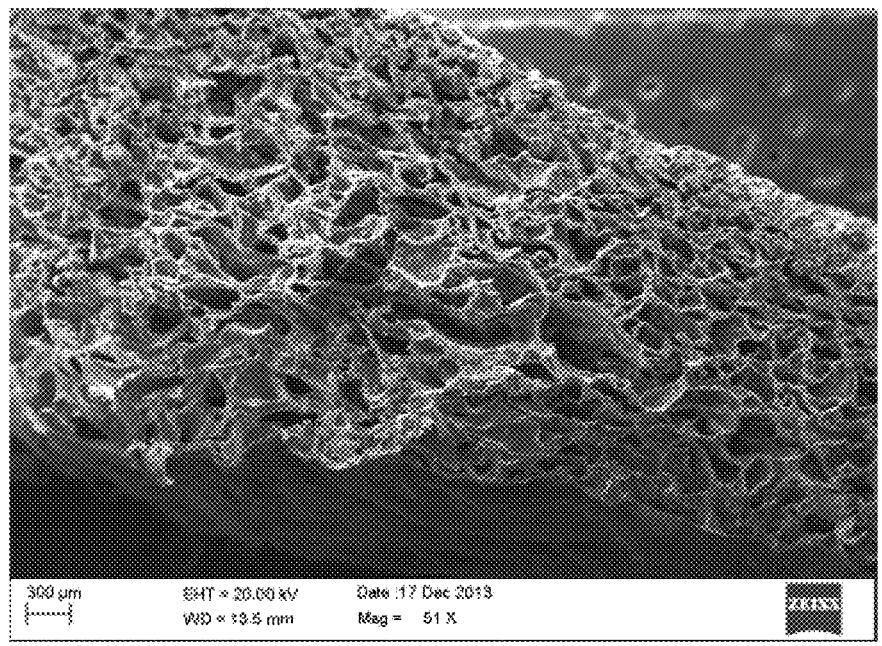
Fig. 6 shows the SEM photograph of the scaffold with loaded drug.

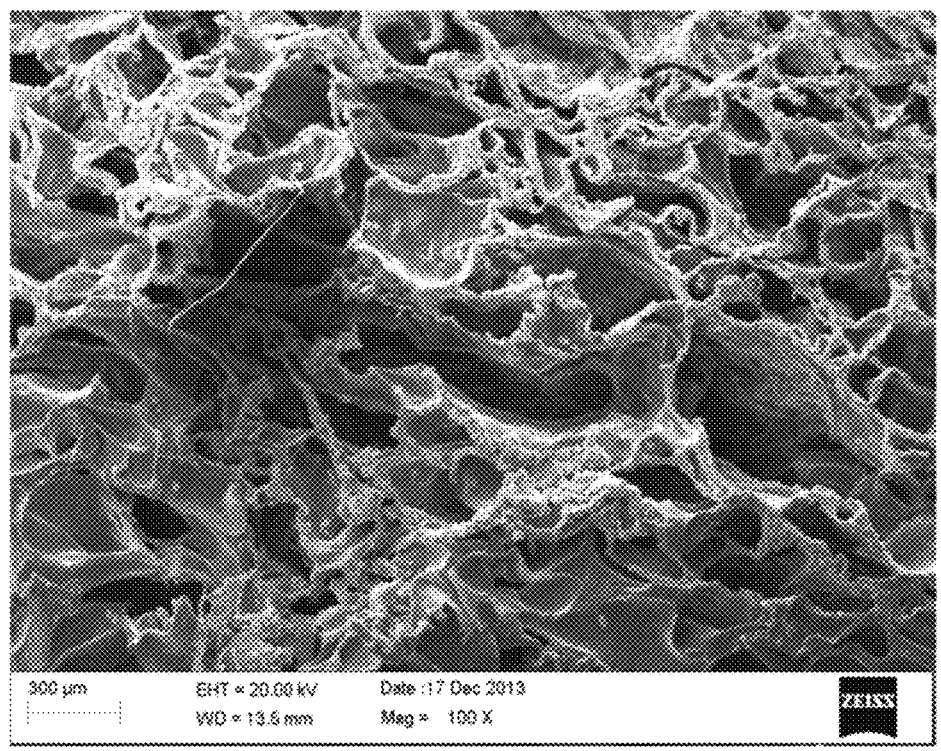
Fig. 7 shows the close magnified SEM photograph of the scaffold with loaded drug.

READY TO USE BIODEGRADABLE AND BIOCOMPATIBLE DEVICE AND A METHOD OF PREPARATION THEREOF

FIELD OF THE INVENTION

The present invention relates to the field of Medical Biotechnology.

Particularly, the present Invention provides a ready to use biodegradable and biocompatible device.

More particularly, the invention relates to a device for wound bleeding stoppage purposes.

Even more particularly, the invention relates to medical nonwoven textiles.

The present invention provides a porous scaffold meant as a therapeutic carrier, more specifically as a Hemostasis product.

The present invention is a sterile wound dressing product to carry the therapeutic and/or bioactive molecules with preference to accelerate the process of stopping bleeding of the wounds.

The present invention also relates to a method of preparing such a device for medical field.

BACKGROUND OF THE INVENTION

Hemostatic products are used to accelerate the process of stopping the bleeding (hemostasis) from surgical or traumatic wounds. Bleeding of the wound may result into loss of blood which in turn may lead to hypovolemic shock leading to tissue and organ damage. In order to stop the bleeding of the wounds several active ingredients like Thrombin, Gelatin, Collagen, Fibrin, Synthetic, etc. are used for manufacturing products which would accelerate the process of stopping the bleeding from wounds. There are several such products known in the art.

Reference may be made to U.S. Pat. No. 8,133,484, titled "Hemostatic materials and dressing" by Preiss-Bloom, et al. dated 13 Mar. 2012. This Invention relates to an adhesive material comprising gelatin and a non-toxic cross-linking material such as transglutaminase. The adhesive material is useful for medical purposes as hemostatic products. The hemostatic products are useful for the treatment of wounded tissue.

Reference may be made to U.S. Pat. No. 8,337,879, titled "Absorbable implants and methods for their use in hemostasis and in the treatment of osseous defects" by Kronenthal dated 25 Dec. 2012. This invention relates to mechanically hemostatic body-absorbable compositions having a putty-like consistency. The compositions preferably comprise a finely powdered, carboxylic acid salt and a liquid block copolymer of ethylene oxide and propylene oxide.

Reference may be made to U.S. Pat. No. 8,252,344, titled "Partially hydrated hemostatic agent" by Hursey dated 28 Aug. 2012. This invention relates to a composition for promoting the formation of clots in blood comprises a zeolite and a binder. The zeolite is adjusted to have a specific moisture content. Processes by which the moisture content is adjusted Include drying, re-hydrating, and combinations of drying and re-hydrating. A method of forming the composition comprises the steps of providing a zeolite and adjusting the moisture content such that upon application of the composition to a wound, a heat of hydration is reduced and heat transferred to the wound is reduced. A method of clotting blood flowing from a wound comprises the steps of applying the zeolite to the wound and maintaining the zeolite in contact with the wound for a predetermined amount of time, the zeolite having adjusted moisture content and being capable of producing a controllable exothermic effect on the wound.

Reference may be made to U.S. Pat. No. 8,668,899, titled "Advanced functional biocompatible foam used as a hemostatic agent for compressible and non-compressible acute wounds" by Dowling, et al. dated 11 Mar. 2014. This Invention relates to a sprayable polymeric foam hemostat for both compressible and non-compressible (intracavitary) acute wounds. The foam comprises hydrophobically-modified polymers, such as hm-chitosan, or other amphiphilic polymers that anchor themselves within the membrane of cells in the vicinity of the wound. By rapidly expanding upon being released from a canister pressurized with liquefied gas propellant, the foam is able to enter injured body cavities and staunch bleeding. The seal created is strong enough to substantially prevent the loss of blood from these cavities. Hydrophobically-modified polymers inherently prevent microbial infections and are suitable for oxygen transfer required during normal wound metabolism. The amphiphilic polymers form solid gel networks with blood cells to create a physical clotting mechanism that prevent loss of blood.

However, none of the products in prior art are as peculiar as the one covered in present invention. The product of present invention is more effective in solving the purpose as discussed above. The present invention provides a single platform for polyelectrolyte complex (to have a combined advantageous features of more than one polymers) to be used as a carrier for multi-therapeuticals (e.g. thrombin, calcium, tranexamic acid to initiate and Intensify the immediate clotting and stabilizing) and other bioactive molecules (e.g. D+Glucosamine to further enhance the platelets and blood cells entrapment). Additionally, this provides a smart executive biomaterial to have even growth promoting effects and antimicrobial feature also. No prior art is available on a device that would satisfy such need. Further, the preparation of the said PEC is achieved using a specifically designed aspect ratio of a system for agitation/homogenization followed by combination of air dry and freeze dry.

However, none of the inventions discussed above comprises of a hemostatic product and a method to prepare the same as covered in the present invention. The distinguishing features of the present invention as compared to prior art discussed above are very significant and prominent, hence the present invention is novel and inventive over the prior, art.

The present invention comprises of a porous scaffold which comprises absorbent gelatin—chitosan polyelectrolyte complex (GCPEC) which is highly porous and impregnated with substances promoting blood clotting. The present invention provides solutions for stopping bleeding quickly and immediately. The device of present invention comprises excellent ventilation features preventing infections which may be caused due to open bleeding wound.

OBJECTS OF THE INVENTION

The main objective of the invention is to provide a device for stopping bleeding immediately and quickly.

Another main objective of the invention is to provide a ready to use biodegradable and biocompatible device.

Another objective of the invention is to provide a method of preparation of such device.

A further objective of the invention is to provide a porous scaffold meant as therapeutic carrier, more specific as a Hemostasis product.

Another objective of the invention is to provide a sterile wound dressing product to carry the therapeutic/bioactive molecules with preference to accelerate the process of stopping bleeding of the wounds.

SUMMARY OF THE INVENTION

The present invention provides a ready to use biodegradable and biocompatible device and a method of preparation thereof. The device of present invention comprises a novel porous scaffold composed of Polyelectrolyte complex (PEC) as carrier of plurality of therapeutics to quickly stop bleeding from any type of wounds, i.e. surgical or non-surgical.

Further the present invention comprises combined application of air dry and freeze dry method in order to develop the device.

The device of present invention comprises of excellent ventilation features which prevents infections which may be caused due to bleeding.

Further the scaffold under the present invention comprises of differential porosity and regulated pores on the same platform in a molecularly integrated PEG matrix.

BRIEF DESCRIPTION OF THE DRAWINGS

FIG. 1 shows the matrix and its micro structure with vesicular voids. The schematic diagram shows the constituents are held in the matrix of DLS Haemostat.

FIG. 2 shows the Schematic representation-Constituents of DLS Haemostat scaffold and the coagulation cascade.

FIG. 3 shows the SEM photographs of the device showing differential porosity and pore size.

FIG. 4 shows the SEM photograph of the scaffold without drug.

FIG. 5 shows the close magnified SEM photograph of the scaffold without drug.

FIG. 6 shows the SEM photograph of the scaffold with loaded drug.

FIG. 7 shows the close magnified SEM photograph of the scaffold with loaded drug.

STATEMENT OF THE INVENTION

Accordingly the present invention provides a ready to use biodegradable and biocompatible device and a method of manufacturing thereof, said device comprising natural porous scaffold micro-matrix based structure mainly of Polyelectrolyte complex (PEC) acting as carrier of plurality of therapeutics and pharmaceuticals to quickly stop bleeding; said matrix based structure comprising of a plurality of polymers and manufactured as a scaffold comprising differential porosity and regulated pores with interconnected small voids on the same platform in a molecularly integrated matrix; such that said device acts as a drug carrier and transporter to supply and transfer said therapeutics and pharmaceuticals into wounds in order to quickly stop bleeding and to reduce ambient contamination, whenever applied on the wound.

DETAILED DESCRIPTION OF THE INVENTION

It should be noted that the particular description and embodiments set forth in the specification below are merely exemplary of the wide variety and arrangement of Instructions which can be employed with the present invention. The present Invention may be embodied in other specific forms without departing from the spirit or essential characteristics thereof. All the features disclosed in this specification may be replaced by similar other or alternative features performing similar or same or equivalent purposes. Thus, unless expressly stated otherwise, they all are within the scope of present invention. Various modifications or substitutions are also possible without departing from the scope or spirit of the present Invention. Therefore it is to be understood that this specification has been described by way of the most preferred embodiments and for the purposes of illustration and not limitation.

The present invention provides a ready to use biodegradable and biocompatible device and method of preparation thereof. The device of present invention is a novel porous scaffold to stop bleeding Immediately and permanently when applied on the wound. The present invention basically relates to the efficient deployment of a biodegradable, biocompatible medical aid through a novel highly porous scaffold that can be deployed at the point of proposed use. The scaffold under the present invention will allow the medical aid with the ability to quickly stop bleeding and also reduce ambient contamination that could cause secondary infection, preserve tissue after injury and facilitate surgical speed.

The present invention is a biodegradable and biocompatible dressing, preferably having chitosan and gelatin as base, for control of traumatic bleeding. The ready-to-use patch under the present Invention consists of a Gelatin and Chitosan foam, impregnated with clotting agents such as but not limited to thrombin, calcium chloride ($CaCl_2$) and Tranexamic Acid. These constituents are held in the vesicular voids of the matrix, on the internal surface of the sponge which are able to act rapidly when blood flows Into the dressing. Once the scaffold under the present Invention is in contact with blood, the dressing enables sealing and stabilization of wound surfaces.

The novel scaffold under the present invention provides an executive and exclusive device for the natural micromatrix composed of Polyelectrolyte complex for carrier of more than one type of therapeutics relating to quickly stop bleeding. Further the present scaffold comprises of combined technology of air dry and freeze dry method which provides excellent ventilation property to the scaffold and exudates absorbency to the scaffold of the present invention.

The present Invention aims to overcome the problems in the existing prior arts and provides the novel and unique features in the scaffold by providing on-demand services for differential porosity and regulated pores on the same platform in a molecularly integrated matrix. The technologies involved are the timed patterned physico-chemical treatment of the two or more polymers viz. gelatin and chitosan using a very simplified process to obtain a stable molecular interaction and orientation between the molecules of at least two of the preferred polymers, which results into a highly porous matrix. The used technology provides the proper interaction and orientation between the functional groups of the polymers used, resulted into a typical polyelectrolyte complex (PEC). The most favourable cation, $NH_3+$, rapidly attracts platelets and erythrocytes in blood flow, initiate coagulation mechanism and form strong blood clots at wound site.

Further under the present invention the novel technology to prepare the scaffold provides two faces to the device. One is more porous with larger pore size and the other is less porous with small pore sizes. The later feature helps to prevent the loss of blood components while the earlier feature allow the blood to enter within the voids of the scaffold resulting into immediate dot generation and migration towards the bleeding site, further interconnected vesicular micro voids hold the drug inside and as a result the encapsulated drugs do not come out of the matrix at significant level.

Further the highly porous structure of the present invention results into Interconnected small voids, provide a large surface area and micro-areas for reactions to occur and thus exert a pseudo-catalytic effect on blood clotting. The whole blood clotting process, the coagulation cascade is activated. The micro-environment aided with drugs viz. thrombin, calcium and tranexamic acid, initiate and intensify the clotting pathway by converting inactive precursor to its active form, so as to form the clot. The co-factor supports the blood clotting process. Anti-fibrinolytic agent in the present invention stabilizes the blood clot and also triggers Intrinsic thrombin generation; hence, prolonged compression is not necessary.

The PEC micro-mesh and body's fibrinogen converted into fibrin forms an efficacious plug and prevents the loss of blood and stops the loss of clotting factor. The novel device of the present Invention makes the product light weighted, to be more physical and also altering the blood clotting mechanism. The scaffold of the present invention can be removed easily usually without causing additional/secondary hemorrhage. The present invention could prevent wound infection due to the antibacterial capability of chitosan.

The novel porous scaffold of the present invention is also capable of being used as a carrier for other therapeutics/ bioactive molecules/cell (primary or stem cell) towards tissue engineering and other biomaterial applications. Moreover, the scaffold of the present invention is also capable of being used as a cover for the compromised tissues either as acellular or cellular product.

The utilization of more than one type of polymer & their properties for multi-therapeutics loaded preparation and impregnation of the same with PEC scaffold, a system for more than one types of the pharmaceuticals (like clotting factors, co-factors, clot stabilizers, antibiotics, analgesics, anti-allergic, antioxidants, growth factors, etc.) to get delivered in phase-wise and controlled manner for extended period of time.

The novel aspect of the present invention Is the sequential timed patterned physico-chemical treatment of the two polymers by using a very simplified process to obtain a stable molecular interaction and orientation between the molecules of the two or more polymers to get highly stabilized porous scaffold without using any cross-linker or any integrated harmful chemicals. Further, the invention comprises of the breakdown of stabilized dried air bubbles and the preparation of said PEC is achieved using a specifically designed aspect ratio of a system for agitation/homogenization. The scaffold matrix of the present invention may comprise of adhesion backing impervious or perforated sheet which would intercalate other matrices in case of large bleeding wound Is to be covered.

The present invention comprises Polyelectrolyte complex porous sponge. The basic structure of the matrix under the present invention Is made from preferably absorbent gelatin-chitosan polyelectrolyte complex (GCPEC) which is highly porous and impregnated with substances promoting blood clotting. The blood clotting process occurs within the voids in the presence of co-factor and clotting factors, further the clot is stabilized by anti-fibrinolytic agent. The porous sponge of GCPEC provides a very large surface area for the flowing blood.

Further the invention comprises of Thrombin which is a plasma protein catalyzing the conversion of fibrinogen into fibrin. This process represents the final phase in the coagulation cascade and leads to the formation of a blood clot. Tranexamic acid is also comprised in the invention which acts as an anti-fibrinolytic agent and stabilizes the blood clot. It also promotes the regeneration of thrombin, and Calcium chloride plays role as clotting factor and supports the coagulation of the blood coming from the wound. This Is also a polymerizing and crosslinking factor for the fibrin, also the Tris buffer is used as a carrier solution for the drugs. Preparation process of the scaffold under the present invention is outlined below in step by step manner:

1. Preparation of Air Dried Samples
   Addition of gelatin in a vessel containing purified water
   Dissolving and Homogenizing the Solution using Stirrer
   Adding chitosan to the acidified solution and homogenizing the mixture
   Casting the homogenized mixture in trays of desired size
   Allowing the sample for air dry
2. Neutralization of Air Dried Samples
   Crushing the samples
   Soaking the crushed sample in neutralization solution
   Washing the samples with water
   Pat dry/vacuum dry
3. Drug Loading and Drying
   Dissolving required drugs and therapeutic chemicals in Tris buffer to load
   Lyophilizing the samples to obtain drug loaded porous scaffold device for use as and when required So, accordingly the present invention provides a ready to use biodegradable and biocompatible device and a method of manufacturing thereof, said device comprising natural porous scaffold micro-matrix based structure mainly of Polyelectrolyte complex (PEC) acting as carrier of plurality of therapeutics and pharmaceuticals to quickly stop bleeding; said matrix based structure comprising of a plurality of polymers and manufactured as a scaffold comprising differential porosity and regulated pores with interconnected small voids on the same platform in a molecularly integrated matrix; such that said device acts as a drug carrier and transporter to supply and transfer said therapeutics and pharmaceuticals into wounds in order to quickly stop bleeding and to reduce ambient contamination, whenever applied on the wound.

In an embodiment, said polymers are preferably selected from but not limited to gelatin, chitosan, collagen, alginate, polyvinyl alcohol, polyurethane, keratin, carboxymethyle cellulose, gelatin hydrolysate, chitosan hydrolysate, partially denatured collagen and/or synthetic or naturally derived molecules such as phytochemicals.

In another embodiment, said therapeutics and pharmaceuticals are selected from but not limited to tranexamic acid, calcium chloride, thrombin and/or glucosamine.

In another embodiment, said scaffold is produced by the steps:
a) preparing a homogeneous solution of the polymers with different ratio in water and acetic acid and subjecting for air drying to obtain an air dried scaffold;
b) cutting and crushing the above obtained air dried scaffold as per requirement and subjecting for the stabilization either by ammonia vapor or ammonia solution or alkali solution;
c) subsequently washing the product as obtained in step (b) with water and squeezing to remove maximum amount of water;

d) loading the required pharmaceutical/therapeutic solution containing different ratio of drugs as per the requirement to the washed porous scaffold to obtain the final ready to use product.

In another embodiment, said method involves physico-chemical treatment of said polymers using a very simplified process in order to obtain a stable molecular interaction and orientation between the molecules of the said polymers, causing an interaction and orientation between the functional groups of the polymers used, resulting into a typical polyelectrolyte complex (PEC), so as to obtain a highly porous matrix.

In yet another embodiment, said matrix comprises of combined application of air dry and freeze dry method.

In another embodiment, said matrix comprises differential porosity and regulated pores with Interconnected small voids, on the same platform in a molecularly integrated matrix with two faces to the scaffold.

In another embodiment, said scaffold provides an executive and exclusive device for the natural micro-matrix composed of Polyelectrolyte complex for carrier of more than one type of therapeutics in order to quickly stop bleeding.

In yet another embodiment, said scaffold is produced through physico-chemical treatment of the polymers using simplified process resulting in a stable molecular interaction and orientation between the molecules of the polymers resulting into a highly porous matrix.

In another embodiment, said scaffold is capable of being used as a carrier for multiple categories of therapeutics and pharmaceuticals and is manufactured as per the requirement.

In another embodiment, said scaffold is efficiently capable of deployment of a biodegradable, biocompatible medical aid that can be deployed at the point of proposed use as per the requirement.

In yet another embodiment, said scaffold comprises of two faces wherein one face is more porous with larger pore size and other face is less porous with small pore sizes.

In another embodiment, said small pores help to prevent the loss of blood components while the large pores allow the blood to enter within the voids of the scaffold resulting into immediate clot generation and migration towards the bleeding site.

In another embodiment, said scaffold comprises of Polyelectrolyte complex i.e. PEC micro mesh where body's fibrinogen converted into fibrin forms an efficacious plug and prevents the loss of blood and stops the loss of clotting factor.

In yet another embodiment, said scaffold comprises interconnected small voids, providing a large surface area and micro-areas for reactions to occur and thus exert a pseudo-catalytic effect on blood clotting.

In another embodiment, said scaffold is capable of being used as a cover for the compromised tissues either as acellular or cellular product.

In another embodiment, said scaffold is capable of delivering pharmaceuticals and therapeutics in phase-wise and systematically controlled manner, for extended period of time, as and when required.

The ready to use biodegradable and biocompatible device and method of manufacturing thereof results in to novel, unique and lightweight scaffold, which also possesses the feature of being removed easily usually without causing additional/secondary hemorrhage.

The ready to use biodegradable and biocompatible device is used to stop the bleeding.

The ready to use biodegradable and biocompatible device is used as carrier for multiple and plurality of therapeutics and cells and also used for tissue repair/regeneration/engineering.

EXAMPLES

The following examples are for the purposes of illustration only and therefore should not be construed to limit the scope of the present invention:

Example 1

Preparation of the air dried samples: First 100 ml of ultrapure water is taken in a beaker. Then 3 gm of gelatin is added in to the beaker containing water and dissolved by heating it. Once the solution is dissolved and heated, it is further Homogenized using stirrer. Then after this 1 ml of Acetic Acid is added and homogenized for 1 min and further 1.5 gm of chitosan is added to the solution and homogenized for 90 min. Once the mixture is homogenized, it Is casted in trays and allowed to air dry. Once the sample is dried, it is cut in to the size e.g. 7 cm*7 cm.

Neutralization of the Air Dried Samples:

The crushed samples are soaked in ammonia solution followed by washing and pat and/or vacuum dry.

Drug Loading and Drying:

50 mM Tris Buffer is prepared and then 490 mg of Tranexamic acid and 98 mg of $CaCl_2$ in Tris buffer are dissolved, further 588 IU of thrombin is added, the final volume is 20 ml. Then the drug solution is loaded to the matrix and lyophilized to obtain drug loaded porous device of the present invention.

Efficacy and Biocompatibility of the Prepared Products were Evaluated Using In-Vitro and In-Vivo Models.

Example 2

In-Vitro Testing of Blood Clotting Efficacy
  Procedure Adopted was Direct Visual Method:
  Clot formation was assessed in tray (~20 $cm^2$ SA) with 4 ml blood thinned by 50% using equal volume of PBS and a 1 $cm^2$ of the product was added to this. A stop watch is started when the test subjects are affected. The clotting time was measured by tilting the tray by more than 45 degree every 30 sec until firm clotting was detected. The time indicated on the watch is the clotting time. These tests were performed in triplicate.

Example 3

In Vivo Efficacy Testing for the Product

The effect of the prepared Hemostat on bleeding was tested in *Capra aegarus hircus* (Domestic Goat). The versions tested are the same in terms of composition and manufacturing quality as the dressings are being used on patients in clinical trials.

Goat was refrained from food the night before the experiment but had free access to water. Animal was anaesthetized by spinal Lignocaine 2%. Noninvasive blood pressure and pulse was monitored by oscillometric method pre and post-surgery. A scalpel was used to create an experimental wound and a wide opening in the femoral artery.

The skin of the inguinal area of the thigh was Incised longitudinally to the groin to expose the femoral artery vasculator. Lidocaine 1-2% was spread on the artery to maximize the dilatation of the vessel. After a brief period of stabilization and recording of baseline data, a uniform incision was made on the femoral artery to induce uncontrolled bleeding. Free bleeding of the puncture site was allowed for 30 seconds followed by application of the cotton gauze (control dressing) or prepared Hemostat for 5 minutes.

The huge uncontrolled bleeding that resulted was stopped completely in a few minutes by pressing a prepared Hemostat onto the bleeding wound. No secondary bleeding occurred, even when the dressing was carefully separated from the wound. However, it was not possible to stop the bleeding with a control dressing (cotton gauze). Furthermore, the physiological parameters of the tested animal were stabilized.

Advantages of the Invention

The present invention stops bleeding within few minutes.
Prevents secondary bleeding.
The scaffold of the present invention does not stick to the wound.
The present invention does not disturb the normal of blood flow.
The present invention comprises of improved wound hygiene.
The scaffold of the present Invention is useful in cases of multiple injury
The present Invention requires less time to stop bleeding and patient can be addressed immediately.
By use of the present scaffold the patient can be transported easily.
The present invention helps in earlier mobilization of the patient,
Ready-to-use bandage for stopping bleeding of wounds and prevents from loss of life due bleeding.
Can be used in surgical procedures including Vascular surgical procedures, accidental and combat field.
Can be manufactured in any size and shape as per the requirement.
Easy to handle.
Interconnected Porous in structure.
Packed in laminated foil pack to protect it from environmental factors (sunlight & moisture).
Thermostat pack (such as Styrofoam) as an insulator and to protect product from getting compressed during transportation or storage.
Multiple bandages can be applied for larger wounds.
Capable of use for at least 24 hours, however, hemostasis achieves within few minutes only.
Can be removed easily without using saline solution or water.
Long Shelf life at ambient temperature. Can be disposed-off by burning or degradation.
Environment friendly as it is degradable easily.

We claim:

1. A hemostat device comprising:
a porous gelatin-chitosan polyelectrolyte matrix structure having opposing first and second porous faces, and a plurality of vesicular voids between said first and second porous faces, the first porous face having pores greater in size than pores in the second porous face;
a clotting agent material carried internally by said plurality of vesicular voids in said porous gelatin-chitosan polyelectrolyte matrix structure and configured to clot blood entering said porous gelatin-chitosan polyelectrolyte matrix structure from said first porous face, the clotting agent material comprising calcium chloride and thrombin;
an anti-fibrinolytic agent carried internally by said plurality of vesicular voids in said porous gelatin-chitosan polyelectrolyte matrix structure and configured to stabilize clotted blood in said porous gelatin-chitosan polyelectrolyte matrix structure without using a cross-linker, the anti-fibrinolytic agent comprising tranexamic acid;
said porous gelatin-chitosan polyelectrolyte matrix structure configured to provide, between the opposing first and second porous faces, a differential and regulated porosity on a same platform in a molecularly integrated matrix;
the pores of the second porous face being configured to prevent loss of blood components, and the pores of the first porous face configured to permit blood to enter the hemostat device; and
a bioactive material carried by said plurality of vesicular voids in said porous gelatin-chitosan polyelectrolyte matrix structure, the bioactive material comprising D+Glucosamine to entrap platelets and blood cells.

2. The hemostat device of claim 1, further comprising an adhesive backing adjacent to said second porous face.

3. The hemostat device of claim 1, further comprising an additional therapeutic agent material carried by said plurality of vesicular voids in said porous gelatin-chitosan polyelectrolyte matrix structure.

4. The hemostat device of claim 3, wherein the additional therapeutic agent material comprises at least one of an antibiotic material, an analgesic material, an anti-allergic agent material, and an antioxidant material.

5. The hemostat device of claim 1 wherein said porous gelatin-chitosan polyelectrolyte matrix structure comprises a polymer selected from the group consisting of: collagen, alginate, polyvinyl alcohol, polyurethane, keratin, carboxymethyl cellulose, gelatin hydrolysate, chitosan hydrolysate, and partially denatured collagen.

* * * * *